US010140420B2

(12) United States Patent
DeVries (10) Patent No.: US 10,140,420 B2
(45) Date of Patent: Nov. 27, 2018

(54) SYSTEMS AND METHODS FOR INDEPENDENT ASSESSMENT OF IMAGE DATA

(71) Applicant: Merge Healthcare Incorporated, Chicago, IL (US)

(72) Inventor: Jon T. DeVries, Cary, NC (US)

(73) Assignee: Merge Healthcare Incorporation, Chicago, IL (US)

( * ) Notice: Subject to any disclaimer, the term of this patent is extended or adjusted under 35 U.S.C. 154(b) by 827 days.

(21) Appl. No.: 13/650,370

(22) Filed: Oct. 12, 2012

(65) Prior Publication Data

US 2013/0094728 A1    Apr. 18, 2013

Related U.S. Application Data

(60) Provisional application No. 61/546,373, filed on Oct. 12, 2011.

(51) Int. Cl.
*G06T 9/00* (2006.01)
*G06F 19/00* (2018.01)

(52) U.S. Cl.
CPC .................................. *G06F 19/321* (2013.01)

(58) Field of Classification Search
CPC ..... G06F 19/321; G06F 19/322; G06Q 50/22; G06Q 50/24; H04L 67/12
See application file for complete search history.

(56) References Cited

U.S. PATENT DOCUMENTS

| 5,040,142 A | * | 8/1991 | Mori | G06Q 10/10 |
| | | | | 715/203 |
| 5,583,758 A | * | 12/1996 | McIlroy | G06F 19/325 |
| | | | | 705/2 |
| 5,606,609 A | * | 2/1997 | Houser | H04L 9/3236 |
| | | | | 382/306 |
| 5,740,428 A | * | 4/1998 | Mortimore | G06F 19/321 |
| 5,835,601 A | * | 11/1998 | Shimbo | G06F 17/24 |
| | | | | 380/29 |
| 5,890,177 A | * | 3/1999 | Moody | G06Q 10/10 |
| | | | | 715/210 |

(Continued)

FOREIGN PATENT DOCUMENTS

WO        WO 9625719 A2 *  8/1996

OTHER PUBLICATIONS

A. L. Belton et al., "Tumour Size Measurement in an Oncology Clinical Trial: Comparison Between Off-site and On-site Measurements", 2003, Clinical Radiology 58, p. 311-314.*

(Continued)

*Primary Examiner* — Gandhi Thirugnanam
(74) *Attorney, Agent, or Firm* — Michael Best & Friedrich LLP (57) ABSTRACT

Systems and methods for managing at least one medical image that includes image data and metadata. One method includes generating, at a processor, a number of copies of the at least one medical image, wherein the number of copies is equal to a number of independent reviewers associated with the at least one medical image. Each of the copies includes the image data and the metadata. The method also includes modifying the metadata of each of the copies to include a unique identifier, and storing the copies to at least one image storage device.

20 Claims, 4 Drawing Sheets

(56) References Cited

U.S. PATENT DOCUMENTS

| | | | | |
|---|---|---|---|---|
| 5,982,956 | A * | 11/1999 | Lahmi | H04N 1/00846 358/401 |
| 6,067,551 | A * | 5/2000 | Brown | G06Q 10/10 |
| 6,175,426 | B1 * | 1/2001 | Hirooka | G06K 15/00 358/1.16 |
| 6,417,870 | B1 * | 7/2002 | Brackett | G06F 19/321 358/1.15 |
| 6,519,632 | B1 * | 2/2003 | Brackett | A61B 8/00 600/437 |
| 7,089,247 | B2 * | 8/2006 | Kloos et al. | |
| 7,102,773 | B1 * | 9/2006 | Oosterhout et al. | 358/1.15 |
| 7,383,462 | B2 * | 6/2008 | Osaki et al. | 714/2 |
| 7,707,043 | B2 * | 4/2010 | Kuth et al. | 705/2 |
| 7,783,072 | B2 * | 8/2010 | Work et al. | 382/100 |
| 7,854,383 | B2 * | 12/2010 | Suzuki | 235/462.01 |
| 7,860,287 | B2 * | 12/2010 | Zahlmann et al. | 382/128 |
| 7,885,825 | B2 * | 2/2011 | Climax et al. | 705/2 |
| 8,005,921 | B2 * | 8/2011 | Ho et al. | 709/217 |
| 8,086,077 | B2 * | 12/2011 | Eichhorn | 382/305 |
| 8,099,307 | B2 * | 1/2012 | Maresh et al. | 705/3 |
| 8,140,350 | B2 * | 3/2012 | Rothpearl et al. | 705/2 |
| 8,200,505 | B2 * | 6/2012 | Walker et al. | 705/2 |
| 8,417,666 | B2 * | 4/2013 | Bailor | G06F 17/24 707/608 |
| 8,825,594 | B2 * | 9/2014 | Skaria | G06Q 10/10 707/608 |
| 2002/0023172 | A1 * | 2/2002 | Gendron | G06F 19/321 709/238 |
| 2002/0191205 | A1 * | 12/2002 | Stringham | G06F 3/1205 358/1.13 |
| 2003/0208378 | A1 * | 11/2003 | Thangaraj | G06F 19/321 705/2 |
| 2004/0001606 | A1 * | 1/2004 | Levy | G06T 1/0021 382/100 |
| 2004/0071038 | A1 * | 4/2004 | Sterritt | G06F 17/30274 365/232 |
| 2004/0143171 | A1 * | 7/2004 | Kalies | G06Q 10/10 600/300 |
| 2004/0143594 | A1 * | 7/2004 | Kalies | G06F 19/363 |
| 2004/0176986 | A1 * | 9/2004 | Kuth | G06F 19/322 705/3 |
| 2005/0044492 | A1 * | 2/2005 | Ramaley | G06Q 10/10 715/255 |
| 2005/0165623 | A1 * | 7/2005 | Landi | G06Q 50/22 705/2 |
| 2005/0185204 | A1 * | 8/2005 | Shelton | H04N 1/00132 358/1.13 |
| 2006/0026034 | A1 * | 2/2006 | Yankelevitz et al. | 705/2 |
| 2006/0159325 | A1 * | 7/2006 | Zeineh | G06F 19/3443 382/128 |
| 2006/0177114 | A1 * | 8/2006 | Tongdee et al. | 382/128 |
| 2006/0242144 | A1 * | 10/2006 | Esham et al. | 707/6 |
| 2006/0253487 | A1 * | 11/2006 | O'Blenis | G06F 17/30722 |
| 2006/0282447 | A1 * | 12/2006 | Hollebeek | G06F 17/30917 |
| 2007/0035759 | A1 * | 2/2007 | Fujimori | 358/1.13 |
| 2007/0046649 | A1 * | 3/2007 | Reiner | 345/173 |
| 2007/0216913 | A1 * | 9/2007 | Toda | 358/1.1 |
| 2007/0271316 | A1 * | 11/2007 | Hollebeek | 707/204 |
| 2007/0283420 | A1 * | 12/2007 | Rantalahti | 726/4 |
| 2007/0291978 | A1 * | 12/2007 | Kim et al. | 382/100 |
| 2008/0052112 | A1 * | 2/2008 | Zahlmann et al. | 705/2 |
| 2008/0059241 | A1 * | 3/2008 | Zahlmann et al. | 705/3 |
| 2008/0175484 | A1 * | 7/2008 | Hartmann et al. | 382/195 |
| 2008/0175515 | A1 * | 7/2008 | Hartmann et al. | 382/289 |
| 2008/0198423 | A1 * | 8/2008 | Ando | G06F 17/30011 358/426.06 |
| 2009/0019360 | A1 * | 1/2009 | Lynggaard et al. | 715/243 |
| 2009/0106331 | A1 * | 4/2009 | Fridman et al. | 707/204 |
| 2009/0226056 | A1 * | 9/2009 | Vlachos et al. | 382/128 |
| 2010/0021027 | A1 * | 1/2010 | Hartkens | G06F 19/363 382/128 |
| 2010/0034376 | A1 * | 2/2010 | Okuizumi et al. | 380/44 |
| 2010/0131873 | A1 * | 5/2010 | Mejia et al. | 715/764 |
| 2010/0228699 | A1 * | 9/2010 | Webber et al. | 707/622 |
| 2010/0303714 | A1 * | 12/2010 | Kirn | 424/1.11 |
| 2011/0059432 | A1 * | 3/2011 | Ballhause et al. | 435/6 |
| 2011/0153361 | A1 * | 6/2011 | Hanina et al. | 705/3 |
| 2012/0224742 | A1 * | 9/2012 | Musser, Jr. | G06T 1/0021 382/100 |
| 2013/0094728 | A1 * | 4/2013 | DeVries | 382/128 |
| 2013/0103425 | A1 * | 4/2013 | Julsrud | 705/3 |
| 2013/0185098 | A1 | 7/2013 | Mitchel et al. | |
| 2014/0112447 | A1 | 4/2014 | Semba | |
| 2014/0142983 | A1 | 5/2014 | Backhaus et al. | |
| 2014/0222444 | A1 | 8/2014 | Cerello et al. | |
| 2014/0297309 | A1 | 10/2014 | Kim et al. | |
| 2014/0350962 | A1 | 11/2014 | Robinson | |

OTHER PUBLICATIONS https://www.inspire.com/groups/talk-psoriasis/discussion/protocol-when-two-specialists-disagree/?ga=freshen, Protocol when two Specialists disagree, author unknown, Sep. 11, 2013, p. 1-18.*

Wang, Fusheng et al., "Towards Building High Performance Medical Image Management System for Clinical Trials", May 20, 2011, Proc SPIE 2011, p. 1-14.*

* cited by examiner

SYSTEMS AND METHODS FOR INDEPENDENT ASSESSMENT OF IMAGE DATA

RELATED APPLICATIONS

This application claims priority to U.S. Provisional Patent Application 61/546,373, filed Oct. 12, 2011, the entire content of which is hereby incorporated by reference.

BACKGROUND

The present invention relates to digital image processing systems and methods. In particular, the invention relates to digital image processing systems and methods for managing medical images.

SUMMARY

Medical images can be acquired for various reasons and uses. Medical images can be acquired for diagnostic and treatment purposes within a hospital setting. In particular, a physician may request that a patient undergo a radiological examination so that the physician can diagnose the patient or track the progress or treatment of a previously-diagnosed issue. In this context, after the images are initially acquired, the images are reviewed by the physician or other healthcare professionals (e.g., a radiologist). The reviewer uses an image viewer to assess the images and make measurements and annotations associated with the images. The reviewer also provides a report summarizing his or her findings, which often includes a dictated narrative. The measurements, annotations, and report are stored and associated with the acquired images. Therefore, if the acquired images are later accessed (e.g., as part of a "second" review or as a standard part of reviewing a patient's health record), the original reviewer's measurements, annotations, and report are available. Making this information available to subsequent reviewers aids informed treatment of a patient based on all available information.

Medical images can also be acquired as part of a clinical trial. For example, during a clinical trial for a new cancer drug, trial participants may undergo one or more radiological examinations to determine how a cancerous tumor reacts to the new drug. Images acquired during a clinical trial are typically handled differently than images acquired in a hospital setting. First, as compared to the non-standard, narrative report generated by a reviewer in a hospital setting, a reviewer in a clinical trial provides an objective quantitative analysis that relies on evidence-based measurements, such as biomarkers. To ensure the accuracy of these objective observations and measurements, images acquired as part of a clinical trial are often blindly reviewed (e.g., in tandem) by at least two reviewers. The results from the reviewers are compared to determine whether the results match. If the results match, the independent assessments are saved for subsequent use and/or review. If the results do not match, one or more additional reviewers may be used to evaluate the images as a tie-breaker. In the end, all of the independent assessments are saved for subsequent use and/or review.

Because images in a clinical trial need to be reviewed blindly by multiple reviewers, systems and methods used to analyze images in a hospital setting are often unusable for clinical trials or require extensive (and costly) modification. Accordingly, many clinical trials rely on manual processes to manage images, which are slow, inefficient, and prone to human errors. Accordingly, embodiments of the invention provide systems and methods for managing image assessment within a clinical trial setting.

In one embodiment, the invention provides a method for managing at least one medical image. The method includes receiving information regarding the at least one medical image, and determining, at a first processor, a number of copies needed of the at least one medical image based on the information regarding the at least one medical image. The method also includes generating, at the first processor, a unique identifier for each copy and providing, to a second processor, the number of copies needed and the unique identifiers. The second processor generates the number of copies of the at least one medical image, modifies each of the copies based on one of the unique identifiers, and stores the copies to at least one image storage device.

In another embodiment, the invention provides a method for managing at least one medical image, wherein the at least one medical image includes image data and metadata. The method includes generating, at a processor, a number of copies of the at least one medical image, wherein the number of copies is equal to a number of independent reviewers associated with the at least one medical image and each of the copies includes the image data and the metadata. The method also includes modifying the metadata of each of the copies to include a unique identifier, and storing the copies to at least one image storage device.

In yet another embodiment, the invention provides a system for managing at least one medical image. The system includes a first processor configured to receive information regarding the at least one medical image, wherein the at least one medical image includes image data and metadata, and to determine a number of copies needed of the at least one medical image based on the information regarding the at least one medical image. The first processor is also configured to generate a number of unique identifiers, the number of unique identifiers equal to the number of copies needed, and to provide, to a second processor, the number of copies needed and the unique identifiers. The second processor generates the number of copies of the at least one medical image, modifies each of the copies to include one of the unique identifiers, and stores the copies to at least one image storage device.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways. It should also be noted that a plurality of hardware and software based devices, as well as a plurality of different structural components may be utilized to implement the invention. Furthermore, and as described in subsequent paragraphs, the specific configurations illustrated in the drawings are intended to exemplify embodiments of the invention and that other alternative configurations are possible.

As described above in the summary section, medical images are used and assessed differently in hospital settings than in clinical trial settings. Within the hospital setting, numerous systems and methods have been developed that match the way images are used and processed. For example, hospitals and other image acquisition sites and networks typically use (1) a Radiology Information System ("RIS") that stores and manages billing, image reports, scheduling, etc. associated with radiological examinations and (2) a Picture Archiving and Communication System ("PACS") that stores and manages the images associated with the radiological examinations. The RIS runs in parallel with the PACS in a streamlined, linear process that automates the standard process of assessing images in a hospital setting. As noted above, the PACS allows individuals to access stored images and any associated annotations, measurements, or reports for a particular radiological examination or a particular patient. Accordingly, as previously noted, although clinical trials also assess medical images, clinical trials often cannot use the standard products and systems used in a hospital setting.

Figure 1:
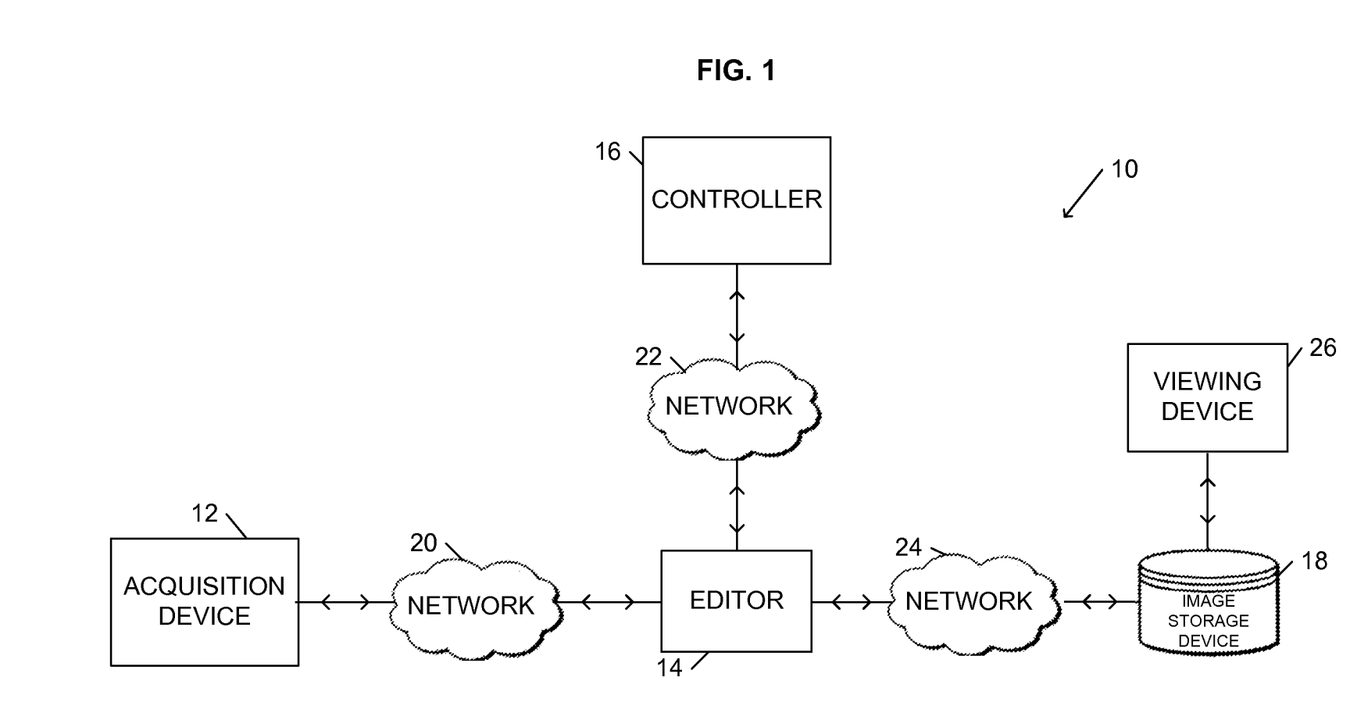
FIG. 1 illustrates a digital image processing system according to one embodiment of the invention.

FIG. 1 illustrates a digital image processing system 10. The system 10 can be used to manage images acquired for a clinical trial. The system 10 includes one or more acquisition devices 12, an editor 14 (e.g., a digital imaging and communications in medicine ("DICOM") editor), a controller 16, and an image storage device 18. As described in more detail below, the acquisition devices 12 acquire digital images of a patient and transmit the images to the editor 14. The editor 14 communicates with the controller 16 to manage the processing of acquired images, which includes storing the images in the image storage device 18. After the images are stored, a reviewer (e.g., an individual reviewing the acquired images for the clinical trial) can use a computing device executing a viewer application (hereinafter referred to as a "viewing device 26") to access stored images. Viewer applications are well-known in the medical image industry and are provided by numerous vendors. The available viewer applications provide different functionality and different compatibility with particular image storage devices 18. In some embodiments, the image storage device 18 includes a PACS, a RIS, and/or a clinical image management system ("CIMS"), which are well-known in the medical industry. Although illustrated as a single device, the image storage device 18 can include multiple devices (e.g., multiple servers or databases).

As illustrated in FIG. 1, a plurality of networks 20, 22, and 24 connect the acquisition devices 12, the editor 14, the controller 16, the image storage device 18, and the viewing device 26. The networks 20, 22, and 24 can include the Internet, a wide area-network ("WAN"), a local-area network ("LAN"), or combinations thereof. The networks 20, 22, and 24 can include wired connections, wireless connections, or combinations thereof. It should be understood that in some embodiments, two or more of the components can be combined into a single system and connected by internal connections as opposed to networks. For example, the controller 16, editor 14, image storage device 18, and viewing device 26 can be connected by internal connections to form a consolidated system for managing images without the need for networks 22 and 24.

Figure 2:
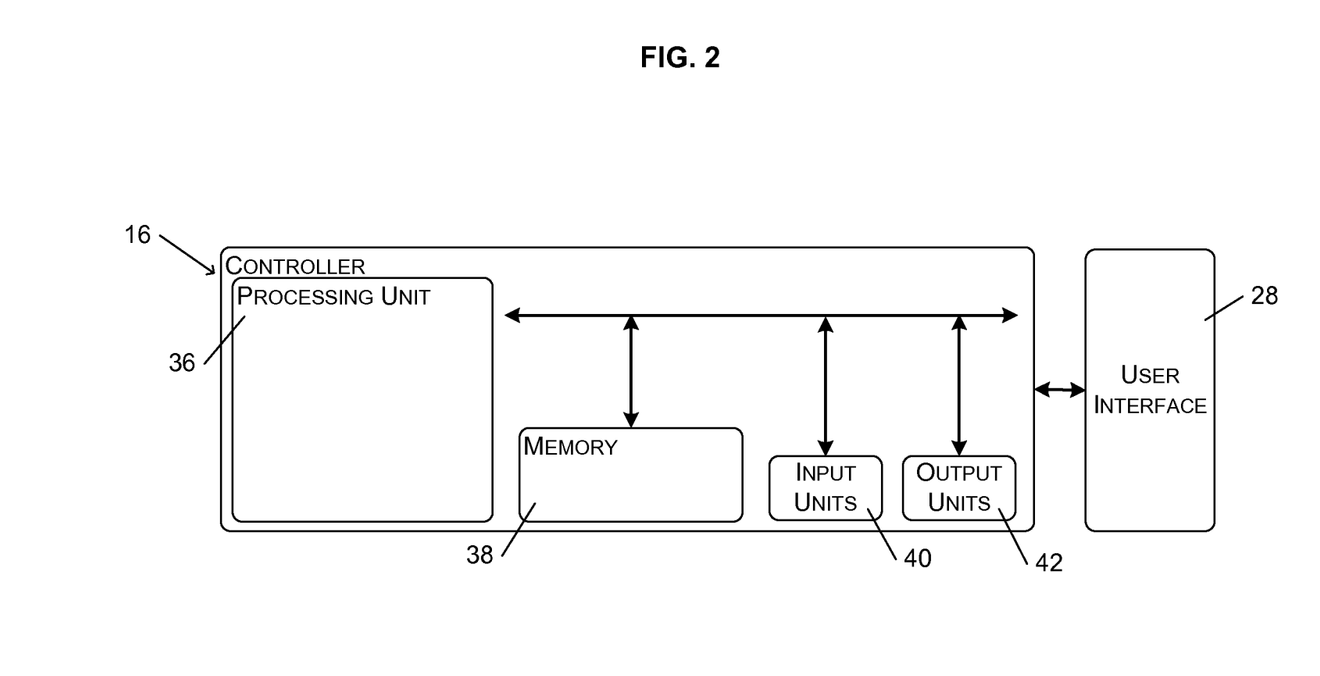
FIG. 2 illustrates a controller included in the digital image processing system of FIG. 1.

As illustrated in FIG. 2, the controller 16 includes at least one processing unit 36 (e.g., a microprocessor, a microcontroller, or another suitable programmable device), one or more non-transitory memory modules 38, one or more input units 40, and one or more output units 42. In some embodiments, the controller 16 includes a combined input/output module in addition to or in place of the separate modules 40 and 42. In addition, alternative configurations of the controller 16 are possible that include more, less, or different components.

The memory module 38 can include one or more types of memory, such as read-only memory ("ROM"), random access memory ("RAM"), flash memory, a hard disk, a removable drive, or other suitable magnetic, optical, physical, or electronic memory devices. As described in more detail below, the controller 16 is configured to retrieve instructions from memory 38 and execute the instructions to manage images. The instructions can include firmware, one or more applications, program data, filters, rules, one or more program modules, and other executable instructions. In some embodiments, the editor 14 is similarly implemented as a software-based device.

As illustrated in FIG. 2, the controller 16 communicates with a user interface 28. The user interface 28 can include a display and input devices such as a touch-screen, a keyboard, a mouse, a plurality of knobs, dials, switches, buttons, etc. As described in more detail below, a user can use the user interface 28 to configure the controller 16 and set parameters for how acquired images are managed and stored for a particular clinical trial.

It should be understood that the components of the system 10 can be combined and distributed in various configurations. For example, in some embodiments, the controller 16 can be combined with the editor 14. Furthermore, the controller 16 can be combined with other systems and devices commonly used in the medical industry, such as an electronic data capture system, a PACS, a RIS, a CIMS or a similar system used to store and manage patient information and subsequent access and processing. For example, in some embodiments, the controller 16 is combined with the image storage device 18, which includes a PACS, RIS, and/or CIMS.

Figure 3:
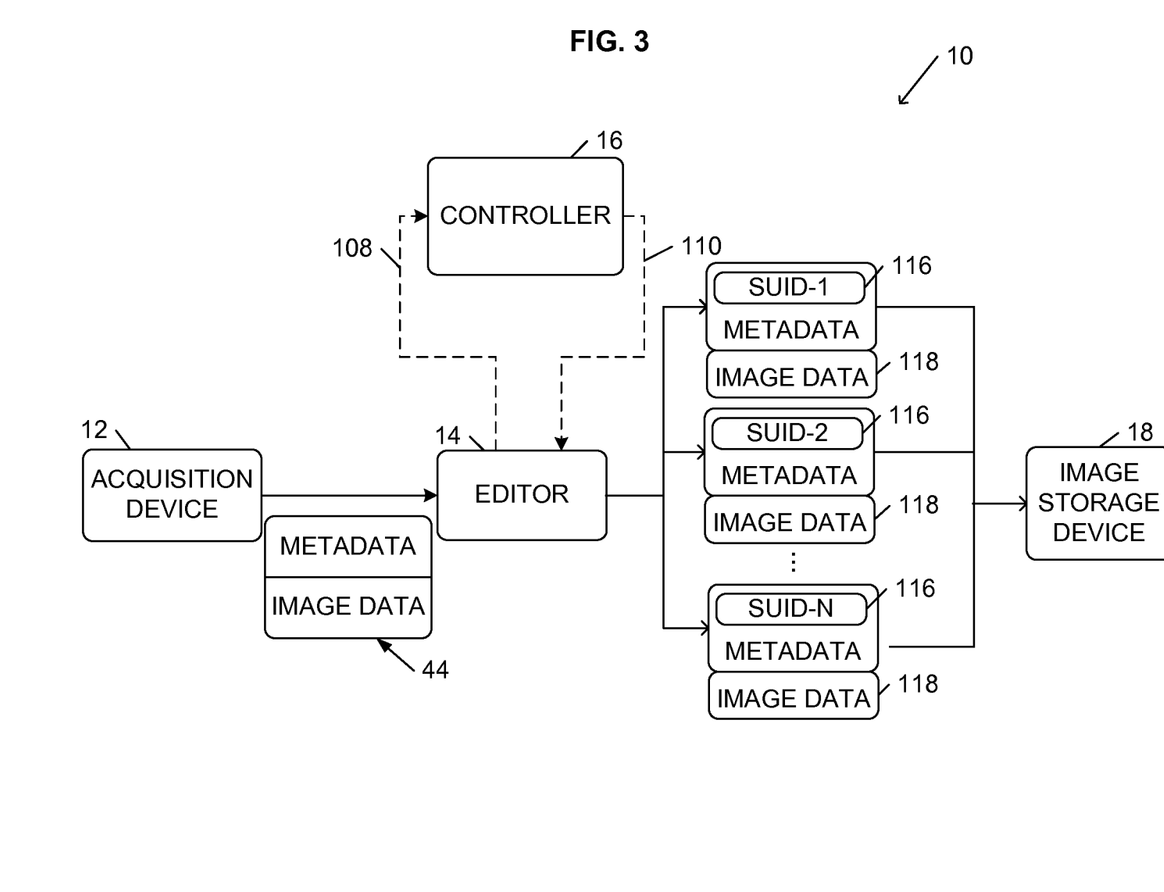
FIGS. 3 and 4 are flow charts illustrating methods performed by the digital image processing system of FIG. 1.

FIG. 3 illustrates a workflow performed by the system 10 for acquiring and managing images. As illustrated in FIG. 3, an acquisition device 12 acquires images and transmits an image object 44 to the editor 14. The image object 44 includes image data (i.e., the digital images captured during a radiological exam by the acquisition device 12) and metadata, which provides information regarding the image data (e.g., patient name, exam date, clinical trial identifier, etc.). In some embodiments, the metadata is contained in a header of the image data.

Figure 4:
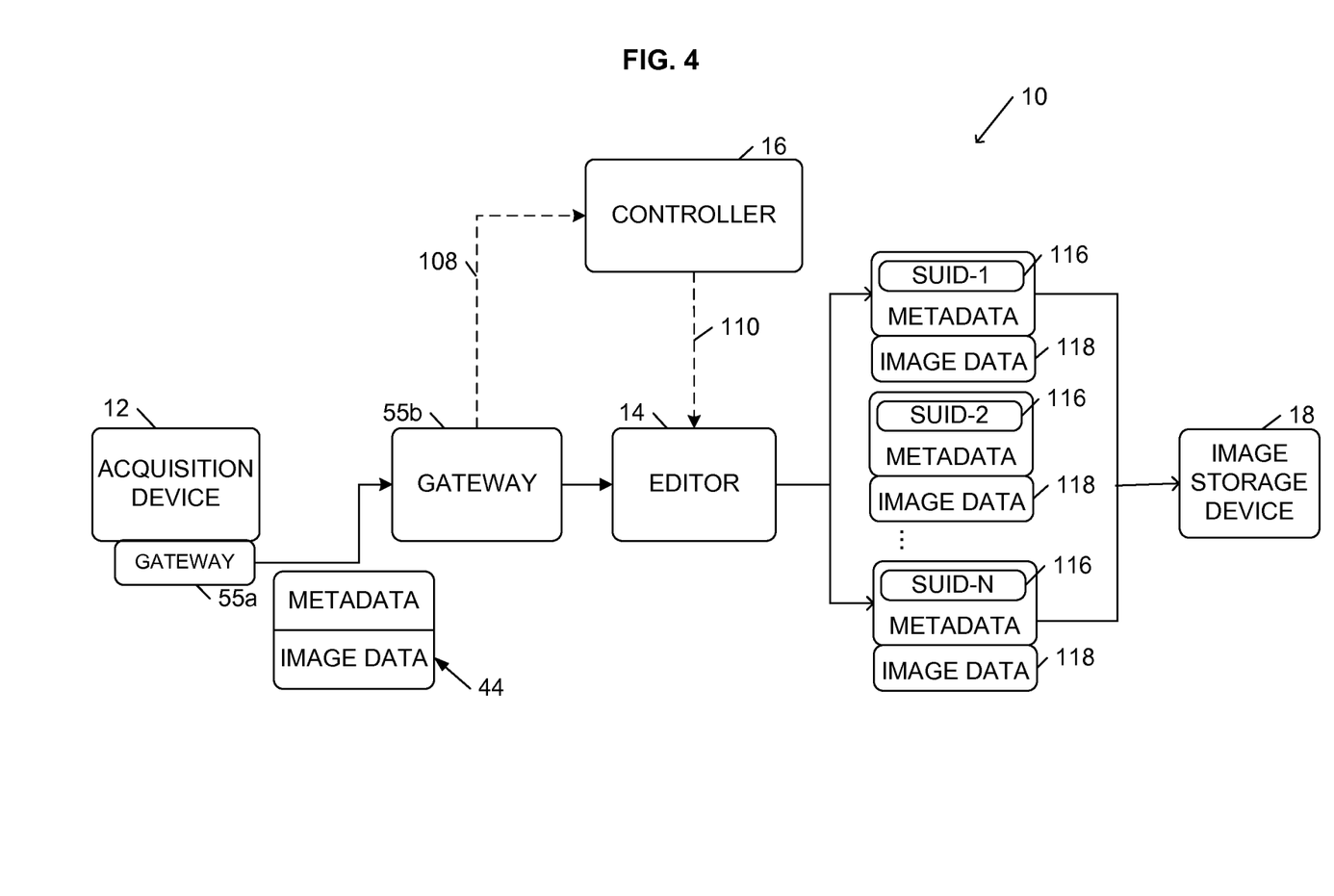

In some embodiments, the metadata is de-identified and standardized before it is transmitted to the editor 14 to comply with industry standards such as the Health Insurance Portability and Accountability Act ("HIPAA"). For example, if the editor 14 is located at a different location than the acquisition device 12, which requires that the image object 44 be transmitted over one or more public or non-secure networks, the acquisition device 12 can de-identify the metadata before transmitting the image object 44 to the editor 14 (e.g., using software installed at the acquisition device 12). In other embodiments, as illustrated in FIG. 4, the system 10 uses a gateway 55 to collect and coordinate the image object 44 to ensure that the image object 44 is compliant with industry standards and regulations (e.g., HIPAA) before the gateway 55 passes the object 44 to the editor 14 for additional processing. Gateways 55 are generally known in the art by various names such as an image gateway or image appliance, and are provided by a number of vendors including, for example, AG Mednet. A gateway can be implemented as an integrated hardware and software device or as a software-based device. For example, as illustrated in FIG. 4, a software-based gateway 55a ("a sending gateway") can be implemented at the acquisition site (e.g., as part of the acquisition device 12) to de-identify the image object 44 and send the image object 44, and a hardware and software gateway 55b ("a receiving gateway") can be implemented at the editor 14 (or as an intermediary device between the sending gateway 55a and the editor 14) to handle receipt of the image object 44. In addition to de-identifying the image object 44, a gateway 55 can provide data security, encrypt and de-crypt the image object 44, and/or compress and de-compress the image object 44. In some embodiments, if the editor 14 is located at or near the acquisition device 12 or the gateway 55, the editor 14 can be configured to perform the de-identification of the image object 44.

The editor 14 is a temporary repository of the image object 44. Once the image object 44 is received by the editor 14, the editor 14 communicates with the controller 16. For example, the editor 14 transmits one or more signals 108 to the controller 16 that notify the controller 16 that the editor 14 has received the image object 44. The signals 108 can include information regarding the received image object 44. For example, in some embodiments, the signals 108 include a clinical trial or subject identifier and other information included in the object's metadata.

Based on the signals 108, the controller 16 determines the clinical trial associated with the image object 44 and determines a number of copies of the image object 44 that is needed. The number of copies can correspond to the minimum number of independent reviewers (e.g., two) used in the determined clinical trial. In other embodiments, the number of copies corresponds to a maximum number of independent reviewers used (e.g., assuming that a tie-breaker may be needed).

To determine the number of copies needed, the controller 16 can access information (stored locally or on an external server or device) that specifies parameters for clinical trials. In some embodiments, a user inputs or sets the parameters for a particular clinical trial using the user interface 28 coupled to the controller 16. The parameters can include a number of independent reviewers (e.g., minimum or maximum) for a particular clinical trial. Upon receiving the parameters from the user through the user interface 28, the controller 16 stores the parameters (e.g., to one or more of the memory modules 38). Therefore, the controller 16 can use the clinical trial identifier included in the signals 108 to determine the clinical trial associated with the received images. The controller 16 can then access the parameters associated with the identified clinical trial to determine the number of copies of the image object 44 needed for the trial.

After determining the number of copies needed for the received image object 44, the controller 16 transmits one or more signals (e.g., processing instructions) 110 to the editor 14. The processing instructions 110 instruct the editor 14 to create a particular number of copies of the received image object 44. For example, the processing instructions 110 can include a number ("N") representing the number of copies needed for the image object 44. The processing instructions 110 can also include a unique identifier for each copy. In particular, to prevent the copies 118 from being exactly identical (which would causes access problems and errors if multiple image objects 44 were stored to the image storage device 18 with identical metadata), each copy 118 needs to be uniquely identifiable. For example, the metadata associated with each copy 118 needs to include at least one piece of information that is different from the metadata of the other copies 118. Therefore, the controller 16 can generate and provide the editor 14 (through the processing instructions 110) a unique identifier for each copy 118. As described below, the editor 14 can modify the metadata for each copy based on one of the unique identifiers provided by the controller 16. In some embodiments, the unique identifier is a value for at least one field included in the image object's header, such as a patient identification field, a medical record number field, a study universal identification number ("SUID") field, and/or an accession number field. It should be understood that the unique identifier can be the value of a single field or the combination of values of multiple fields. For example, the unique identifier can be a combination of the value of a trial identification field (similar to a patient identification field in a hospital setting) and the value of the medical record number field, SUID field, or accession number field.

Therefore, the editor 14 receives the processing instructions 110 and creates N copies 118 of the image object 44. The editor 14 also modifies the metadata associated with each copy 118 based on of the unique identifiers provided by the controller 16. For example, the metadata of each copy 118 includes at least one field 116, such as the SUID field illustrated in FIGS. 3 and 4, and the editor 14 sets the field 116 of each copy 118 to one of the unique identifiers provided by the controller 16. Accordingly, although each copy 118 includes most of the same data as included in the original image object 44 (e.g., the image data and metadata associated with administrative data, such as patient demographics, acquisition site information, etc.), each copy 118 is identifiable as a unique image object based on the information included in the field 116.

After creating the copies 118 and modifying the copies 118 based on the unique identifiers, the editor 14 transmits the copies 118 to the image storage device 18 for storage (e.g., as image objects 44). In some embodiments, the editor 14 discards the original image object 44 and does not transmit the original image object 44 to the image storage device 18. In other embodiments, the editor 14 transmits the original image object 44 to the image storage device 18 with the copies 118 or transmits the original image object 44 to a second storage location separate from the image storage device 18. It should be understood that the functionality of the controller 16 and the editor 14 described above can be combined and distributed in various ways. For example, in some embodiments, the editor 14 generates the unique identifier for each copy 118 rather than the controller 16. In other embodiments, the controller 16 generates the copies 118 and supplies the copies 118 to the editor 14, and the editor 14 assigns the unique identifiers and stores the copies 118 to the image storage device 18. Furthermore, in some embodiments, the controller 16 is combined with the editor 14 and the functionality of each component as described above is provided by a single system or device.

Because the copies 118 have unique identifiers (e.g., field 116), the image storage device 18 stores and treats each copy 118 as a unique image object 44 (i.e., a unique study or exam) that can be independently accessed, and measurements, observations, and other annotations made to one copy 118 do not affect the other copies 118. Accordingly, the image storage device 18 can include standard, unmodified devices or products, such as a PACS, RIS, and/or CIMS, while still providing blind review for a clinical trial.

Although the image storage device 18 treats the copies 118 independently, the controller 16 can store information that associates the copies 118 with the original image object 44 (e.g., metadata from the original image object 44 and the unique identifiers assigned to the copies 118), such that the controller 16 can track the copies 118 made from the original image object 44. Accordingly, the controller 16 can provide information to individuals or other computing devices or systems regarding what image objects stored to the image storage device 18 are copies of the same original image object. This information can be used by the controller 16 or other computing devices or systems to reconcile assessments (e.g., compare independent assessments of images and request tie-breakers as needed). This information can also be used to alert particular reviewers when images are available for review. In particular, the controller 16 can provide a reviewer with a unique identifier associated with a particular image object stored in the image storage device 18 (e.g., a value for the field 116), and the reviewer can access the image from the image storage device 18 using the provided identifier and the viewing device 26. In some embodiments, the controller 16 can be configured to provide the unique identifier automatically to a particular reviewer. In other embodiments, the controller 16 can provide this information to individuals who manually inform the reviewers. In still other embodiments, the controller 16 can provide this information to other computing devices or systems that use the information to alert reviewers of available images.

Upon receiving a unique identifier for a stored image object, a reviewer can access the image object stored in the image storage device 18 using the viewing device 26. As noted above, because the image storage device 18 can include standard image management systems and devices, such as a RIS, PACS, and/or CIMS, the viewing device 26 can execute any standard viewer application compatible with the image storage device 18. Accordingly, the system 10 can be used to access images without requiring customized viewer applications.

Upon accessing an image object, the reviewer can provide measurements and annotations of the image data (hereinafter referred to as an "image assessment"). The image assessment can be saved with the image object in the image storage device 18. For example, in some embodiments, the image assessment is stored as part of the object's metadata. In other embodiments, the assessment is stored in a separate file, database, or server. However, even when the image assessment is stored separately from the image storage device 18, the assessment is linked to the associated object (e.g., based on the unique identifier included in the field 116 of the object). Therefore, the image assessment can be subsequently retrieved with the object.

Because each copy 118 is associated with a different unique identifier, even if one reviewer completes his or her review of their copy 118 in tandem with another reviewer, each reviewer is assessing a different copy 118. Furthermore, without having the unique identifiers of the other copies 118, each reviewer cannot access the assessments generated by the other reviewers of the other copies 118. Therefore, the reviewers remain blind to the assessments performed by other reviewers. The controller 16, however, retains the information necessary to link the copies 118 created for a particular original image object 44. The controller 16 can use this information to reconcile the independent assessments (e.g., compare the assessments to determine if a tie-breaker assessment is necessary) and manage review of each copy 118. It should be understood that the controller 16 can store the information necessary to link the copies 118 in the memory 38 or in a separate memory accessible by the controller 16 (e.g., over a direct connection or a network). Furthermore, in some embodiments, a component different from the controller 16 accesses the information linking the copies 118 and uses the information to reconcile the independent assessments or otherwise manage review of each copy 118.

In some embodiments, the system 10 also provides quality control to check for and correct various errors that can occur during a clinical trial. For example, in some cases an image object is received that uses various names for the same pathology or anatomy or an acquisition site sends too many series. In these cases, a quality control technologist would edit the exam or image object so that it complies with the clinical trial parameters. These changes need to be included in all of the copies created for the image object. If the quality control function takes place before the image object 44 reaches the editor 14, the editor 14 copies the image object 44 that already includes the quality control changes. Alternatively, if the quality control function takes place after the editor 14 copies the object, the editor 14 (based on information supplied from the controller 16) can update each of the previously-generated copes to include the quality control changes.

It should be understood that the components of the system 10 can be arranged in various configurations. For example, the editor 14 and the controller 16 can be included in the same location or alternatively, the controller 16 can be at a remote location with respect to the editor 14. Additionally, the editor 14 and the image storage device 18 can be included in the same location or alternatively, the image storage device 18 can be at a remote location with respect to the editor 14. Furthermore, as noted above, the system 10 may include a database or server other than the image storage device 18 to store image assessments. In addition, one or more of the above-described components can be hosted, such as in a "cloud" environment. For example, in some embodiments, the controller 16 is hosted but is configured to receive and provide information regarding acquired images and corresponding copies as described above. However, it should be understood that any combination of the components described herein may be hosted.

It should also be understood that, although systems and methods described herein are used in the context of managing medical images associated with a clinical trial, these systems and methods may be used for other applications. For example, the systems and methods described herein can be used in any application that requires independent blind or tandem review of images, such as for teaching or student evaluation purposes or for providing second opinions.

Thus, the invention provides, among other things, a system and method for creating and managing data objects that are independently retrievable for independent assessment. Various features and advantages of the invention are set forth in the following claims.

What is claimed is:

1. A method for managing at least one medical image, the method comprising:
   receiving information regarding the at least one medical image, the information including a clinical trial identifier associated with the at least one medical image;
   determining, at a first processor, a number of copies needed of the at least one medical image based on the clinical trial identifier associated with the at least one medical image;

generating, at the first processor, a unique identifier for each copy;

storing metadata from the at least one medical image and the unique identifier for each copy;

linking, at the first processor, the unique identifier for each copy with the metadata from the at least one medical image to indicate which copies are generated based on the at least one medical image;

de-identifying the at least one medical image prior to generating the number of copies of the at least one medical image; and providing, to a second processor, the number of copies needed and the unique identifiers, wherein the second processor generates the number of copies of the at least one medical image, modifies the metadata of each of the copies based on one of the unique identifiers, and stores the copies to at least one image storage device, and wherein each medical image includes an image object, and wherein generating the unique identifier for each copy includes generating a unique value for at least one field of a header of the image object.

2. The method of claim 1, further comprising receiving, through a user interface, parameters associated with a clinical trial and storing the parameters.

3. The method of claim 1, wherein determining the number of copies needed includes assessing parameters associated with a clinical trial.

4. The method of claim 1, wherein determining the number of copies needed includes determining a number of independent reviewers associated with a clinical trial.

5. The method of claim 4, wherein determining the number of independent reviewers includes determining a minimum number of independent reviewers associated with the clinical trial.

6. The method of claim 4, wherein determining the number of independent reviewers includes determining a maximum number of independent reviewers associated with the clinical trial.

7. The method of claim 1, wherein generating the unique value for the at least one field includes generating a unique value for a study universal identification field.

8. The method of claim 1, wherein generating the unique value for the at least one field includes generating a unique value for at least one of a patient identification field, a medical record number field, and an accession number field.

9. The method of claim 1, further comprising providing each of the unique identifiers to a different reviewer, each unique identifier allowing a reviewer to access and review one of the copies independently of the remaining copies.

10. The method of claim 1, further comprising accessing an image assessment associated with each copy that is linked to the at least one medical image and comparing the image assessments of the copies linked to the same at least one medical image to determine when additional image assessments are needed.

11. A system for managing at least one medical image, the system comprising:
a first processor configured to:
receive information regarding the at least one medical image, the at least one medical image including image data and metadata, the information including a clinical trial identifier associated with the at least one medical image;
determine a number of copies needed of the at least one medical image based on the clinical trial identifier associated with the at least one medical image;
generate a number of unique identifiers, the number of unique identifiers equal to the number of copies needed; and
provide, to a second processor, the number of copies needed and the unique identifiers,
link the unique identifier for each copy with the metadata from the at least one medical image to indicate which copies are generated based on the at least one medical image, and
store the unique identifiers and the information regarding the at least one medical image to associate the unique identifiers with the at least one medical image,
wherein the second processor de-identifies the at least one medical image prior to generating the number of copies of the at least one medical image, generates the number of copies of the at least one medical image, modifies the metadata of each of the copies to include one of the unique identifiers, and stores the copies to at least one image storage device, and
wherein each medical image includes an image object, and wherein the unique identifiers each include a unique value for at least one field included in each image object.

12. The system of claim 11, further comprising a user interface coupled to the first processor, the user interface configured to receive parameters associated with a clinical trial from a user and provide the parameters to the first processor.

13. The system of claim 12, wherein the first processor stores the parameters to at least one non-transitory memory module.

14. The system of claim 13, wherein the first processor is configured to determine a number of copies needed of the at least one medical image by accessing the parameters stored in the at least one non-transitory memory module.

15. The system of claim 11, wherein the number of copies needed equals a number of independent reviewers of the at least one medical image.

16. The system of claim 11, wherein the at least one field includes at least one of a unique value for a study universal identification field, a patient identification field, a medical record number field, and an accession number field.

17. The system of claim 11, wherein the first processor is further configured to provide each of the unique identifiers to a different reviewer, each unique identifier allowing a reviewer to access and review one of the copies independently of the remaining copies.

18. The system of claim 11, wherein the first processor is further configured to access an image assessment associated with each of the copies that include unique identifiers associated with the at least one medical image, and compare the image assessments of the copies associated with the at least one medical image to determine when additional image assessments are needed.

19. The system of claim 11, further comprising the second processor, the second processor configured to temporarily store the at least one medical image and provide the information regarding the at least one medical image to the first processor.

20. The system of claim 11, wherein the at least one image storage device includes at least one of a radiology information system, a picture archiving and communication system, and a clinical image management system.

* * * * *